US006544186B1

(12) United States Patent
Shelby et al.

(10) Patent No.: US 6,544,186 B1
(45) Date of Patent: Apr. 8, 2003

(54) SYSTEM AND METHOD FOR DIAGNOSTIC IMAGING

(75) Inventors: Jerod O. Shelby, West Richland, WA (US); Barbara A. Fecht, Richland, WA (US); Todd F. Garlick, Pasco, WA (US); George F. Garlick, Richland, WA (US); Victor I. Neeley, Kennewick, WA (US)

(73) Assignee: Advanced Imaging Technologies, Inc., Preston, WA (US)

( * ) Notice: Subject to any disclaimer, the term of this patent is extended or adjusted under 35 U.S.C. 154(b) by 0 days.

(21) Appl. No.: 09/988,839

(22) Filed: Nov. 19, 2001

(51) Int. Cl.[7] .................................................. A61B 8/14
(52) U.S. Cl. ...................... 600/463; 600/437; 600/445; 600/444; 600/447
(58) Field of Search ................................ 600/445, 463, 600/437, 444, 447; 73/599–642

(56) References Cited

U.S. PATENT DOCUMENTS

| | | | |
|---|---|---|---|
| 3,564,905 A | 2/1971 | Brenden et al. .............. 73/67.5 |
| 3,742,439 A | 6/1973 | Sheridon ................... 340/5 H |
| 3,879,989 A | 4/1975 | Brenden .................. 73/67.5 H |
| 3,911,729 A | 10/1975 | Collins ................... 73/67.5 H |
| 3,983,529 A | 9/1976 | Langlois .................... 340/5 H |
| 4,028,934 A | 6/1977 | Sollish ..................... 73/67.8 S |
| 4,206,763 A | * 6/1980 | Pedersen .................... 128/915 |
| 4,478,481 A | 10/1984 | Fusek et al. ................ 350/3.83 |
| 4,531,410 A | 7/1985 | Crostack ....................... 73/603 |
| 4,662,222 A | 5/1987 | Johnson ........................ 73/602 |
| 5,179,455 A | 1/1993 | Garlick .......................... 359/9 |
| 5,212,571 A | 5/1993 | Garlick et al. .................. 359/9 |
| 5,235,553 A | 8/1993 | Garlick et al. .................. 367/7 |
| 5,329,202 A | 7/1994 | Garlick et al. .............. 310/334 |
| 5,329,817 A | 7/1994 | Garlick et al. ................ 73/605 |
| 5,562,095 A | * 10/1996 | Downey et al. ............. 128/916 |
| 5,796,003 A | 8/1998 | Sandhu et al. ................ 73/603 |
| 5,999,836 A | 12/1999 | Nelson et al. .............. 600/407 |
| 6,056,692 A | * 5/2000 | Schwartz ..................... 600/443 |
| 6,210,331 B1 | * 4/2001 | Raz ............................ 600/443 |

* cited by examiner

Primary Examiner—Francis J. Jaworski
Assistant Examiner—William C. Jung
(74) Attorney, Agent, or Firm—Seed IP Law Group PLLC

(57) ABSTRACT

An imaging system and method provides for the automatic leveling of a hologram detector system. A detector system must be precisely oriented in a proper predetermined orientation. The present invention senses the orientation of a plate to which the detector system is mounted and adjusts driver motors to maintain the detector system at a desired predetermined orientation. In an exemplary embodiment, orientation sensors form a feedback loop to a servo controller to control the position of the motors and thus maintain the detector system at the predetermined orientation. In another aspect of the invention, the patient table may be repositioned with respect to the imaging system. The patient is positioned on a table and imaging performed. If an object of interest is detected, the patient table may be independently repositioned in three orthogonal directions such that the object of interest coincides with an axis of rotation of the patient table. In this manner, the object of interest stays within a predetermined focal plane as the patient is rotated such that the object may be viewed from various angles.

16 Claims, 10 Drawing Sheets

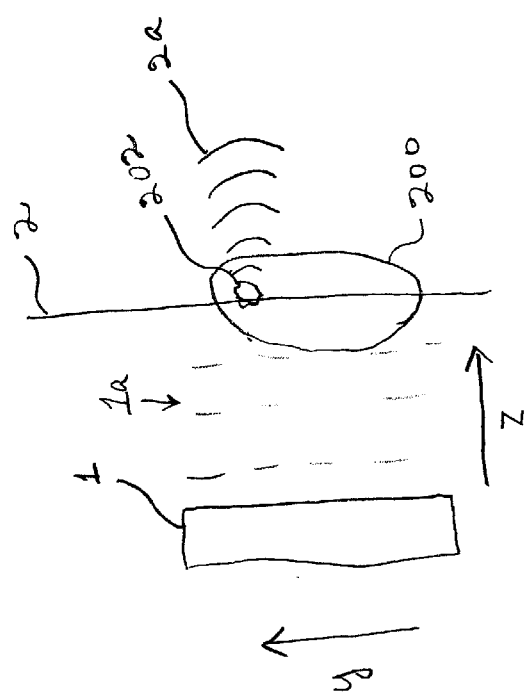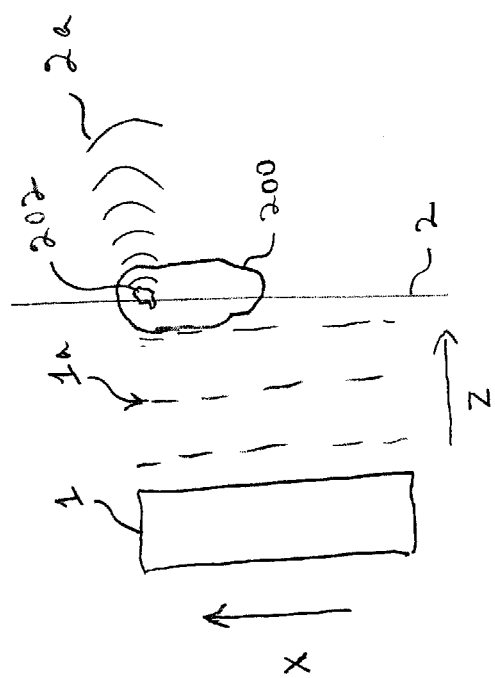

SYSTEM AND METHOD FOR DIAGNOSTIC IMAGING

BACKGROUND OF THE INVENTION

1. Field of the Invention

The present invention is directed generally to apparatus, methods and procedures for improved diagnostic imaging and, more particularly, to a system and method for improved reliability and patient comfort in diagnostic imaging.

2. Description of the Related Art

Breast cancer screening techniques have concentrated on the process of mammography because screening technique need to be economical in order to achieve widespread use. However mammography often has a high incidence of false positive readings that often prove to be benign or fluid-filled cysts that do not require surgical intervention or other highly invasive therapeutic procedures. It is widely accepted that late-stage breast cancer detection is associated with significantly increased morbidity and mortality. Despite extensive research, new diagnostic classification systems and improved detection methodologies, there is still a great need to detect small neoplasms (typically 5 mm or smaller) accurately, quickly, noninvasively and inexpensively and with a good idea of size during the early detection process. Failure to detect such early breast cancers is associated with more invasive therapeutic interventions at higher risk and higher expense.

One alternative to X-ray mammography is conventional, reflective ultrasound using a pulse-echo technique. Generally, breast sonograms using reflective ultrasound are used to characterize masses (such as whether they are cystic or solid) detected by physical exam or by mammography. There is still debate within this field whether reflective ultrasound is able to accurately predict benign from malignant solid masses. Moreover, reflective ultrasound is operator-dependent and time-consuming. Further, sonography is not useful for the assessment or detection of micro calcifications, often the only sign of early in situ ductal carcinomas.

Another alternative is to use a through transmitted plane wave of ultrasound energy to pass through the anatomy and thus carry with it the phase and amplitude information about the anatomy. This, however, is a complicated set of data since it represents three-dimensional information of the internal structure of the anatomy. A demonstrated method of converting this set of dynamic data into a useful image is through the use and application of acoustical holography as disclosed in the referenced prior art patents and patent applications.

Ultrasonic holography as typically practiced is illustrated in FIG. 1. A stimulus wave of sound 1a (i.e., ultrasound) is a plane wave that is generated by a large area object transducer 1. Such a transducer is described in U.S. Pat. No. 5,329,202. The sound is scattered (i.e., diffracted) by structural points within the object. The scattered sound 2a from the internal object points that lie in the focal plane 2 are focused (i.e., projected) into a hologram detector plane 6 of a hologram detector 7. The focusing is accomplished by an ultrasonic lens system 3, which focuses the scattered sound into the hologram detector plane 6 and the unscattered sound into a focal point 4. U.S. Pat. No. 5,235,553 describes an ultrasonic lens that may be satisfactorily used for the ultrasonic lenses illustrated as the lens system 3 in FIG. 1. The ultrasonic lens system 3 also allows the imaging process to magnify the image (i.e., zoom) or change focus position. U.S. Pat. No. 5,212,571 illustrates a lens system that can magnify the image and change focus position and may be used satisfactorily for the lens system 3.

Since the focal point 4 of the unscattered sound is prior to the hologram detector plane 6, this portion of the total sound again expands to form the transparent image contribution (that portion of the sound that transmitted through the object as if it were transparent or semi-transparent). In such an application, an ultrasound reflector 5 is generally used to direct the object sound at a different angle, thus impinging on the hologram detector plane 6, which usually contains a liquid that is deformed by the ultrasound reflecting from the liquid-air interface. In an exemplary embodiment, The base of the hologram detector 7 is made to be parallel with the ground so that the thickness of the fluid below hologram plane 6 remains at a constant value.

When a reference wave 8 and the object wave are simultaneously reflected from the hologram detector 7, the deformation of the liquid-air interface is the exact pattern of the ultrasonic hologram formed by the object wave (1a combined with 2a) and the "off-axis" reference wave 8. This ultrasonic hologram formed on the detector plane 6 is subsequently reconstructed for viewing by using a coherent light source 9, which may be passed through an optical lens 10, and reflected from the holographic detector plane 6.

This reflected coherent light contains two components. The first component is light that is reflected from the ultrasound hologram that was not diffracted by the ultrasonic holographic pattern, which is focused at position 11 and referred to as undiffracted or zero order light. The second component is light that does get diffracted from/by the ultrasonic hologram is reflected at an "off-axis" angle from the zero order at position 12 and referred to as the "first order" image view when passed through a spatial filter 13. It is noted that this reconstruction method produces multiple diffraction orders each containing the ultrasonic object information. Note also both + and − multiple orders of the diffracted image are present and can be used individually or in combinations to view the optical reconstructed image from the ultrasonically formed hologram by modifying the spatial filter 13 accordingly. The hologram detector 7, coherent light source 9, optical lens 10, and spatial filter 13 may be referred to in combination as a detector system 15.

It is apparent from the understanding of the operation of acoustical holography that the anatomy of the patient needs to be inserted into the path of the acoustical energy that is referred to as the object wave. Furthermore, the system must remain stable during operation. The present invention provides this and other advantages as will be apparent from the following detailed description and accompanying figures.

SUMMARY OF THE INVENTION

The present invention is embodied in a system and method that improves reliability and simplifies operation of diagnostic imaging. In one aspect, the invention is embodied in a system for stabilizing an image detector that is configured to receive acoustic signals and comprises a base member and a mounting platform fixedly coupled to the base member. A leveling plate supports the image detector and a plurality of adjustable leveling members having first and second ends couple the leveling plate to the mounting platform. The first end of each leveling member is coupled to the mounting platform and the second end of each leveling member is coupled to the leveling plate. A level sensor assembly detects an orientation of the leveling plate and generates sensor signals related thereto. A controller responds to the sensor signals to generate leveling control signals and a drive mechanism coupled to at least a portion of the leveling members responds to the leveling control signals to position the leveling plate at a predetermined orientation.

In an exemplary embodiment, the level sensor assembly and drive mechanism form a feedback circuit. The level sensor assembly may comprise first and second level sensors that are positioned in a substantially orthogonal arrangement on the leveling plate to sense variations in the first and second substantially orthogonal directions.

In another aspect, an imaging system generates an image of patient anatomy and has a predetermined area of imaging coverage and is focused at a predetermined focal plane. The system comprises a three-dimensional drive system to control position of the patient in three dimensions with the drive system operating in two dimensions to position a selected anatomical feature of the patient at a desired location within the predetermined area of imaging coverage and operating in a third dimension to position the selected anatomical feature of the patient at a desired plane substantially parallel with the predetermined focal plane. The system further comprises a rotational drive system to permit rotation of the selected anatomical feature about an axis of rotation substantially within the desired plane wherein the selected anatomical feature is imaged within the predetermined area of imaging coverage and about the axis of rotation.

In one embodiment, the imaging system may comprise an ultrasound imaging system or may be used with an x-ray imaging system.

In another aspect, the imaging system has an adjustable focus and is readjusted such that the readjusted focal plane coincides with the desired plane. This allows the selected anatomical feature to be viewed as the rotational drive system rotates the anatomical feature.

BRIEF DESCRIPTION OF THE DRAWINGS

FIG. 4 is a side view of an imaging system generating a plane wave to interact with an object.

FIG. 5 is a top view of an imaging system generating a plane wave to interact with an object.

DETAILED DESCRIPTION OF THE INVENTION

The present invention provides a technique of positioning the patient such that the anatomy of interest can be placed in the imaging acoustic wave while maintaining a comfortable position for the patient. This invention further provides for repositioning the patient while maintaining the anatomy in the imaging field. Such repositioning allows for the rotation of the patient, and thus the anatomy around the center of the imaging position of interest, thereby providing additional three-dimensional information about the anatomy. This repositioning further provides for the patient to be transferred from a kneeling position to a horizontal position while providing direct access to the anatomy without losing the continuity of imaging the anatomy. This invention also addresses a novel approach to maintaining stability with patient movement by means of an automatic leveling system for the imaging system.

Figure 1:
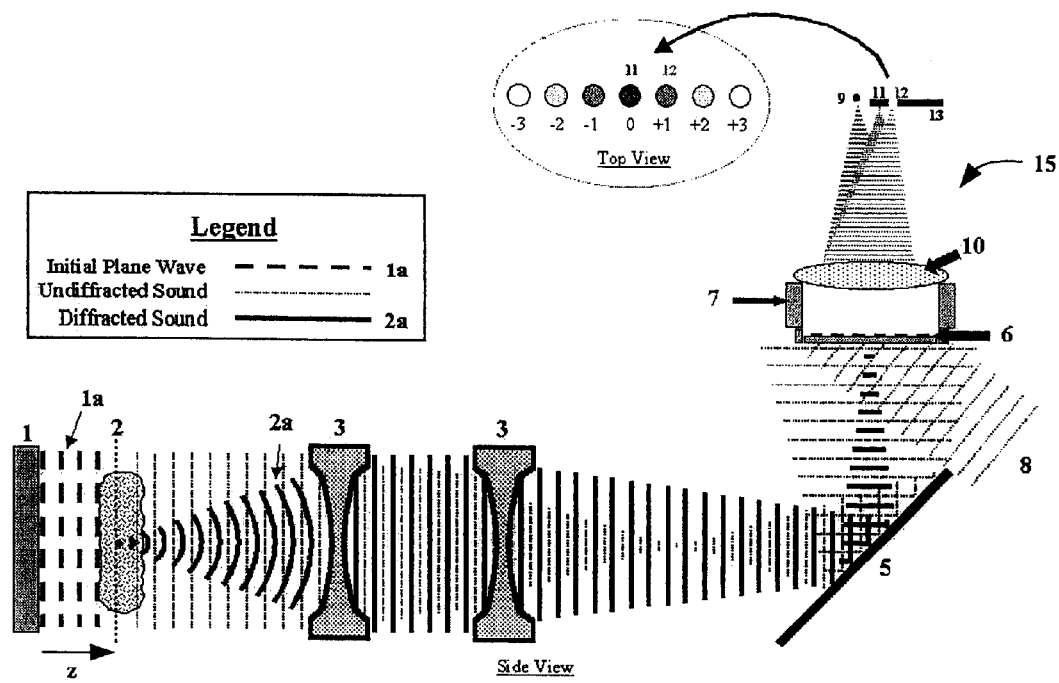
FIG. 1 is a functional block diagram illustrating the operation of a conventional through-transmitted wave acoustic ultrasound holography.

When the patient is placed in position for diagnostic imaging, the weight of the patient or other external forces on the system may alter the orientation of the hologram detector 7 (see FIG. 1). With a liquid surface detector, such as illustrated in FIG. 1, it is desirable that the hologram detector 7 be maintained in a horizontal orientation so the liquid maintains a uniform distribution within the hologram detector. A further need for maintaining the detector alignment is that if the hologram detector 7 (see FIG. 1) is misaligned then the spatial filtering structure 11–13 is no longer positioned around a line perpendicular to the liquid surface since the liquid surface will align to gravity and thus no longer be parallel with the hologram detector 7. The net result is that the reflected image information will no longer or only partially pass through the spatial filter 12 (see FIG. 1). Ideally, it is desirable that the hologram detector 7 be maintained in a horizontal orientation with the tolerance of ±0.004 degrees. Those skilled in the art will appreciate that such precise alignment is difficult even in the absence of a patient. However, when a patient is positioned for diagnostic imaging, the weight of the patient on the exam table or chair may be sufficient to cause misalignment in the hologram detector. Further, as the diagnostic imaging machine is operated and the patient moved, misalignment of the conventional detector may occur.

Figure 2:
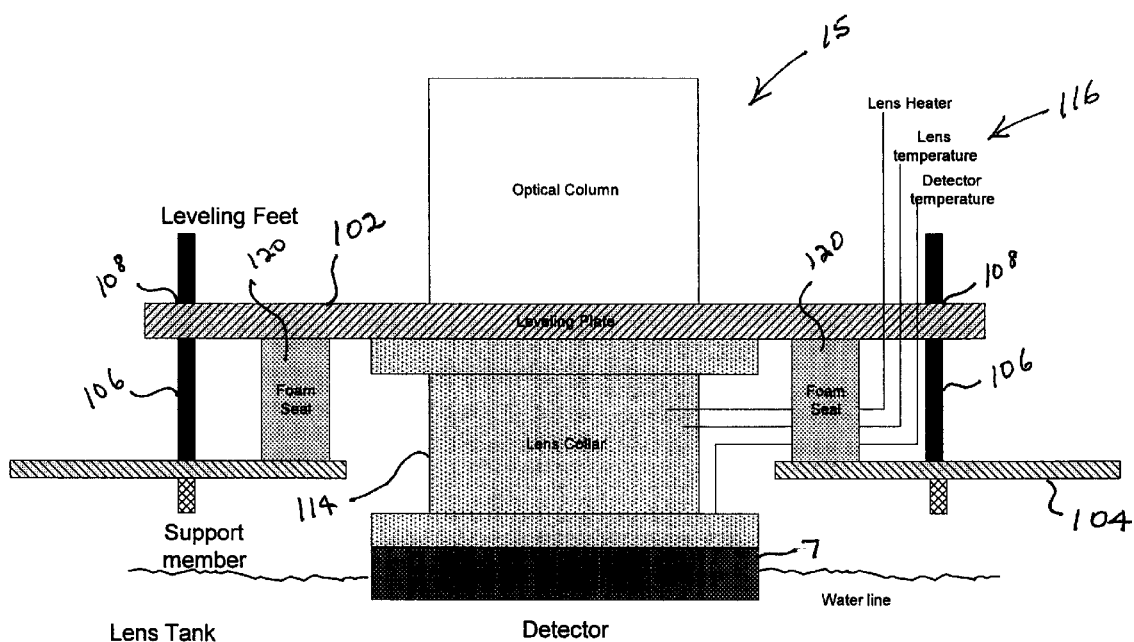
FIG. 2 is a side view illustrating the placement of the image detector and the automatic leveling system.
Figure 3:
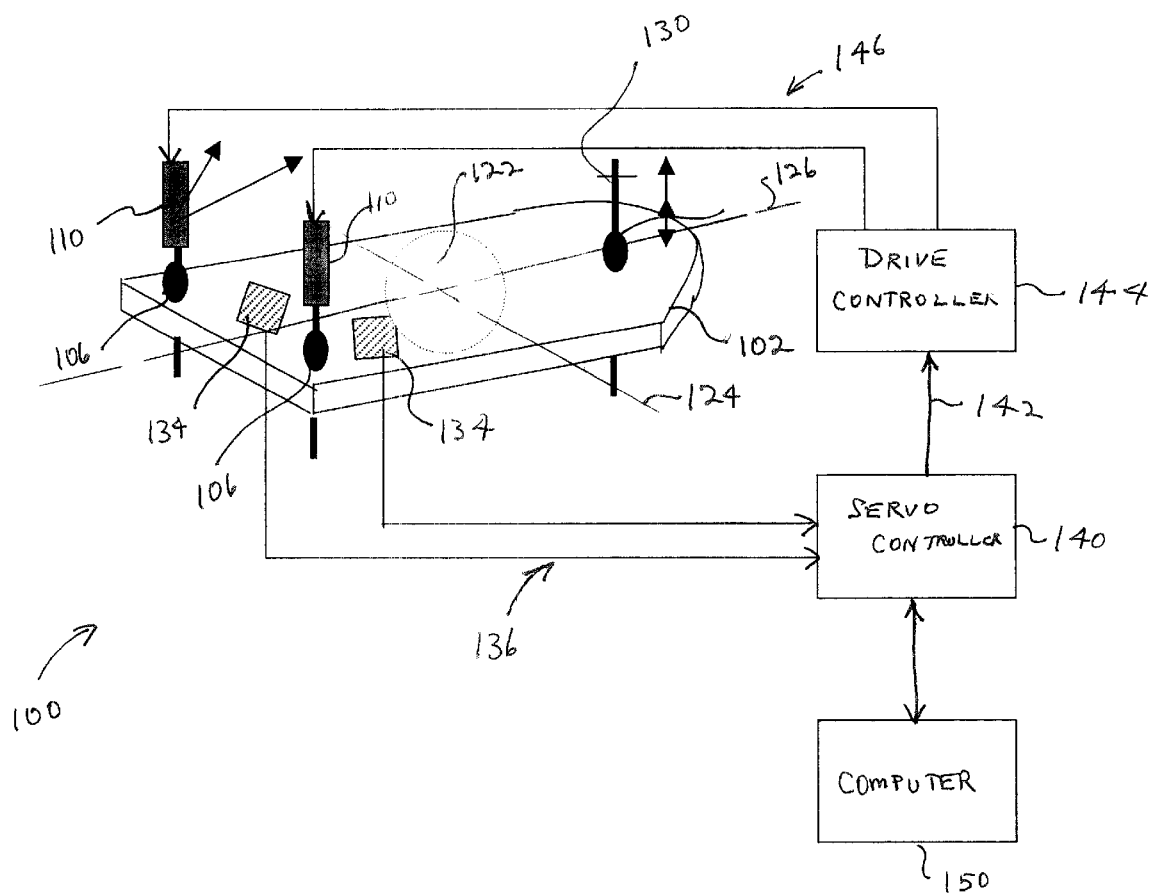
FIG. 3 is a schematic illustrating the operation of the system in one aspect to automatically level an image detector.

The present invention, illustrated in the functional diagrams of FIGS. 2 and 3, automatically adjusts the hologram detector 7 to compensate for variations in alignment that may occur as a result of patient loading and other factors. The present invention is embodied in a system 100 illustrated in FIG. 2 and includes a leveling plate 102 upon which the hologram detector 7 is mounted. A base plate or support member 104 is fixedly mounted. For example, the base plate 104 may be mounted to a water tank (not shown) in which the transducer 1 (see FIG. 1) and lens system 3 are mounted. Alternatively, the base plate 104 may be attached to a rigid support member (not shown) that may be mounted directly to the system 100 or to the floor. The base plate 104 must be sufficiently rigid and have sufficient strength to support the leveling plate 102 and the attached detector system 15 (see FIG. 1).

The spacing between the leveling plate 102 and the base plate 104 is controlled by a set of leveling feet 106. In an exemplary embodiment, the leveling feet 106 may be implemented by finely threaded rods having, by way of example, approximately 80 threads per inch. The leveling feet 106 are rotatably mounted at a first end to the base plate 104 using conventional technology, such as recessed area or mounted ring with the feet are positioned within the center.

An intermediate portion of the leveling feet 106 is inserted through threaded holes 108 in the leveling plate 102. A second end of the leveling feet 106 are coupled to driver motors 110, illustrated in FIG. 3. The leveling feet 106 are attached to the shaft of the driver motors 110 for rotation therewith. As the driver motors 110 rotate, the leveling plate 102 is raised or lowered a corresponding amount. In this manner, the precise orientation of the leveling plate 102 may be maintained at a predetermined desired orientation, such as horizontal.

The optical lens 10 (see FIG. 1) may be mounted within a lens collar 114, which is fixedly coupled to the hologram detector 7. The lens collar 114 may include conventional elements, such as a temperature element and lens heater as well as a temperature sensing element to detect the temperature of the hologram detector 7. These control elements 116 are known in the art and need not be described in greater detail herein. Also illustrated in FIG. 2 is a foam seal 120, positioned between the leveling plate 102 and the base plate 104. The foam seal 120 provides an environmental seal and it may also serve to dampen vibrations of the detector system 15.

For the sake of clarity, other portions of the detector system, such as the coherent light source 9 and spatial filter 13 are not shown in FIG. 2 since this aspect of the invention is directed to a technique for automatically adjusting the orientation of the leveling plate 102. FIG. 3 illustrates the leveling plate 102 with the detector system 15 removed. FIG. 3 illustrates an aperture 122 through which the detector system 15 is inserted.

The leveling plate 102 may be manufactured from a rigid material, such as aluminum or steel. As best illustrated in FIG. 3, the leveling plate 102 is elongated in shape and has a short axis 124 and a long axis 126. The leveling feet 106 are mounted at a first end of the leveling plate 102 at a distance substantially equidistant from the long axis 126. At an opposite end of the leveling plate, a manual leveling foot 130 is used to adjust the overall height of the leveling plate 102 with respect to the base plate 104. That is, the leveling foot 130 is adjusted to control the overall height while the leveling feet 106 automatically adjust to maintain the proper orientation of the leveling plate 102 at the desired predetermined orientation. The location of the leveling feet 106 at locations equidistant from the line axis 126 allows adjustment of the leveling plate in substantially two orthogonal directions. That is, the leveling feet 106 may be adjusted to orient the leveling plate about the long axis 126 or in an orientation parallel to the short axis 124.

The system 100 includes orientation sensors 134 to sense the orientation of the leveling plate 102. In an exemplary embodiment, the orientation sensors 134 may be capacitor fluid-type detectors, which have a sensitivity as small as ±0.001 degrees, which is satisfactory for use in the system 100. In an exemplary embodiment, the orientation sensors 134 are oriented in substantially orthogonal directions to sense the orientation of the leveling plate in directions parallel to the short axis 124 and the long axis 126, respectively. That is, one orientation sensor 134 is used to sense the orientation in one direction, such as parallel to the short axis 124, while the other orientation sensor 134 senses the orientation of the leveling plate 102 in a direction, such as parallel to the long axis 126.

The orientation sensors 134 generate electrical signals 136 indicative of the orientation of the leveling plate 102. The electrical signals 136 are coupled to a servo controller 140. The servo controller 140 may be a commercial standalone device manufactured with analog or digital circuitry, or may comprise a processor, such as microprocessor, microcontroller, digital signal processor, or the like. The operation of the servo controller 140 is within the scope of knowledge of one of ordinary skill in the art. Accordingly, the specific operational details of the servo controller 140 need not be provided herein.

The servo controller 140 generates control signals 142 based on the electrical signals 136 from the orientation sensors 134. The control signals 142 are coupled to a drive controller 144. The drive controller 144 may be readily implemented using conventional elements, such as motor control circuitry. The specific implementation of the drive controller 144 depends on the selected device used to implement the driver motors 110. In an exemplary embodiment, the driver motors 110 may be stepper motors. In this embodiment, the drive controller 144 may comprise conventional stepper motor controllers. A stepper motor may be advantageously used to control the displacement of the leveling feet 106 by transmitting a number of pulses from the drive controller 144 to one or both of the driver motors 110. Those skilled in the art will recognize that motor drive signals 146 from the drive controller 144 may be used to move the driver motors 110 in either direction to raise or lower the leveling plate 102. One of the driver motors 110 may go in one direction while the other driver motor 110 goes in the opposite direction.

The orientation sensors 134 combined with the servo controller 140, drive controller 144, and driver motors 110 form a closed loop servo system. The electrical signals 136 generated by the orientation sensors 134 provide a feedback signal to the servo controller 140. In response to the feedback signals, the servo controller 140 generates control signals 142 that operate the drive controller 144. The drive controller 144 generates the motor drive signals 146 to control the position of the driver motors 110. Thus, a feedback loop automatically adjusts the orientation of the leveling plate 102 to maintain it at a constant predetermined orientation, such as a horizontal orientation.

It is desirable that the driver motors 110 operate quickly to adjust for variations in the orientation that may result, by way of example, from the patient being placed on the imaging system. The weight of the patient may be sufficient to cause misorientation of the detector system 15. However, in the presence of the feedback loop control system of the system 100, the orientation of the leveling plate 102 and thus the detector system 15 is automatically controlled. The nature of the detector may be such that in general it will not respond to high frequency forces or vibrations thus the response speed of the motors 110 often can be slow with corrections being on a one second time interval. In other applications the response speed is required to be rapid and the provision to reduce over correction as discussed below must be incorporated.

Although quick response time is desirable, those skilled in the art will recognize that feedback loops have inherent instabilities if a loop response time is too high. Conventional loop damping techniques may be used to prevent runaway operation of the servo loop and to avoid instability around the predetermined orientation of the leveling plate. If the servo controller 140 is implemented with a digital system, the servo controller may simply generate control signals 142 at a predetermined rate, such as once per second. Once the leveling plate 102 (and the attached detector system 15) are at the proper predetermined orientation, the servo controller 140 may generate control signals 142 less frequently. If the servo controller 140 is implemented with analog circuitry, a proportional integral derivative control loop may be used where the integration time effectively controls the loop response.

The system 100 advantageously provides for automatic orientation adjustment of the leveling plate 102 and the attached detector system 15. Those skilled in the art will recognize that other implementation details may be provided yet remain within the scope of the invention. For example, the orientation sensors 134 may be implemented with other known forms of technology. Similarly, the driver motors 110 may be implemented with other known devices, such as conventional DC motors or hydraulic controls. Other materials may be substituted for the leveling plate 102, the base plate 104, and the leveling feet 106.

The servo controller 140 may be coupled to a computer 150, which controls the imaging apparatus. The servo controller 140 may provide an indication to the computer 150 that the orientation of the leveling plate (and the attached detector system 15) are at the desired predetermined orientation. Thus, the computer 150 receives information indicating that the detector system 115 is properly aligned in that the imaging may occur. The system 100 may provide an interlock so that the computer 150 does not begin the imaging process until the leveling plate 102 and attached detector system 15 are in the proper orientation. This prevents the unnecessary operation at the imaging system until the detector system 15 is in the desired predetermined orientation.

Figure 6:
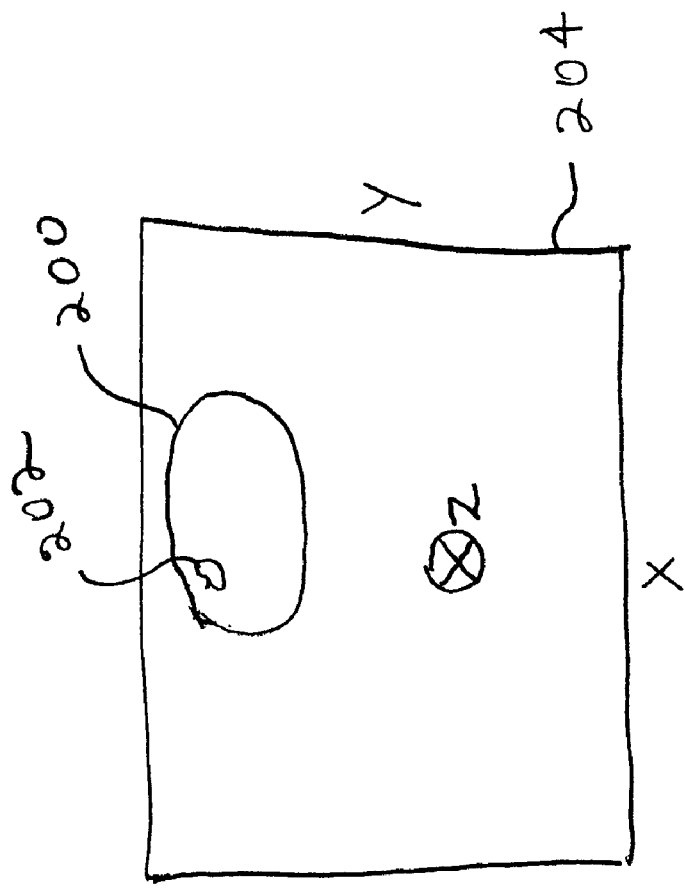
FIG. 6 is a view of an object to be imaged and contained within a two-dimensional area of coverage of the imaging system.

In another aspect of the system 100, it is desirable to control the orientation of the patient during the imaging process. For purposes of the following discussion, it is convenient to consider the system 100 as operating in a three-dimensional Cartesian coordinate system having 3 orthogonal directions indicated as x, y, and z. As previously discussed, the stimulus wave 1a generated by the transducer 1 may be considered a plane wave in the x-y plane. In the side view of FIGS. 1 and 4, the direction of propagation of the ultrasound stimulus wave 1a is indicated by a reference arrow z. Thus, the side view illustrated in FIG. 4 illustrates the propagation of the stimulus wave 1a in the y-z plane. The top view of FIG. 5 is viewed in the x-z plane and illustrates the propagation of the stimulus wave 1a in the z direction. Finally, FIG. 6 illustrates the operation of the system 100 in the x-y plane. The transducer 1 produces the stimulus wave 1a having a coverage area 204 that is best illustrated in FIG. 6. The direction of propagation, indicated by the reference z, is illustrated, using conventional physics terminology, as the rear portion of an arrow. The x-y plane of FIG. 6 is taken the focal point 2, illustrated in FIGS. 4 and 5.

For the sake of convenience, the transducer 1 is illustrated in FIGS. 4–6 as a single transducer generating the stimulus wave 1a that propagates along an axis corresponding to the direction z. Such a large area transducer is known from U.S. Pat. No. 5,329,202, assigned to the assignee of the present invention and incorporated herein by reference in its entirety. Alternatively, multiple transducers may be used, such as described in U.S. Pat. No. 5,329,817, assigned to the assignee of the present invention, and incorporated herein by reference in its entirety. The multiple transducers may generate plane waves that propagate in the direction z or may generate plane waves at an angle θ with respect to the z-axis. Although such off-axis stimulation is known, it is more convenient for purposes of the present invention to illustrate the stimulus wave 1a as propagating in the direction of the z-axis. The present invention is not limited to a specific form of the transducer 1. Indeed, as will be discussed in greater detail below, the present invention is applicable to signal sources other than acoustic ultrasound signals.

In each of the FIGS. 4–6, an anatomical object 200 of a patient to be imaged is placed in the path of the stimulus wave 1a. The object 200 must be positioned within the coverage area 204 to be imaged by the system 100. In certain examples presented herein, the anatomical object 200 may be a breast when the system 100 is used for breast cancer screening or other diagnostic measures. The anatomical object 200 may contain a lesion or structure 200 that interacts with the stimulus wave 1a. As previously discussed, the interaction may include reflection, refraction, and diffraction. The scattered sound 2a is directed towards an image detector, such as, by way of example, the detector system 15. However, the present invention may be utilized with detectors other than a liquid surface detector. For example, the patient orientation system of the present invention may be utilized with a solid state detector or other ultrasound detector device known in the art.

When a structure 202 is imaged, it is desirable to identify and classify the structure as a benign structure, or other structure requiring additional study and/or biopsy. The classification of various structures is well understood by medical doctors and is not required for proper understanding of the present invention.

FIGS. 4–6 illustrate the imaging of a structure 202 at the focal plane 2. However, as is known in the art, the lens system 3 (see FIG. 1) may be altered to produce an image in the x-y plane at a different focal plane. Thus, the lens system 3 permits imaging in the z-axis as well. Such an imaging process to determine the dimensions of lesions is described in U.S. patent application Ser. No. 09/507,559, filed on Feb. 18, 2000, now allowed, which is assigned to the assignee of the present invention and which is incorporated herein by reference in its entirety.

Figure 7:
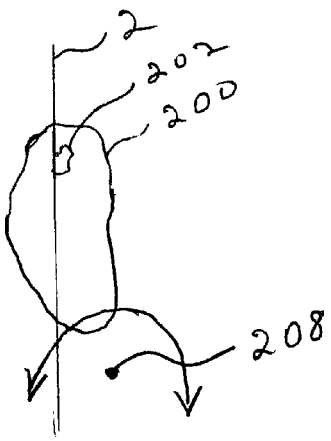
FIG. 7 is a top view of an imaged object illustrating a focal plane and an axis of rotation.
Figure 8:
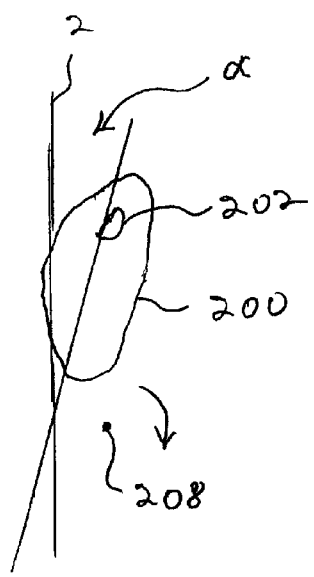
FIG. 8 illustrates the movement of the object to be imaged out of the focal plane when rotated along the axis of rotation.

Additional diagnostic information may be available by viewing the structure 202 from various angles. However, it is inconvenient to move the imaging system with respect to the patient. The transducer 1 and lens system 3 are generally in large water tanks and thus cannot be readily repositioned. Accordingly, it is desirable that the system provide for rotation of the patient to view the structure 202 from various angles. A difficulty encountered in such rotation is that the structure 202 will move out of the focal plane 2 as the patient is rotated. This is illustrated in FIGS. 7 and 8. In FIG. 7, the structure 202 is within the focal plane 2. An axis of rotation is indicated by a reference 208. As can be seen, the axis of rotation 208 is in the y-plane. As the object 200 is rotated about the axis of rotation 208 by an angle α, the structure 202 moves out of the focal plane 2. Thus, the structure 202 can no longer be properly imaged since it is no longer within the focal plane 2.

The present invention advantageously permits rotation about the axis 208 while maintaining the structure within the focal plane 2. This is accomplished by providing the mechanism that allows the object 202 to be moved so that it coincides with the axis of rotation 208. As can be seen from FIG. 9, as the patient is rotated, the structure 202, which coincides with the axis of rotation 208, remains within the focal plane 2. This permits the diagnostician to examine the structure 202 from various angles, thus providing additional data for the identification and/or classification of the structure 202.

Figure 10:
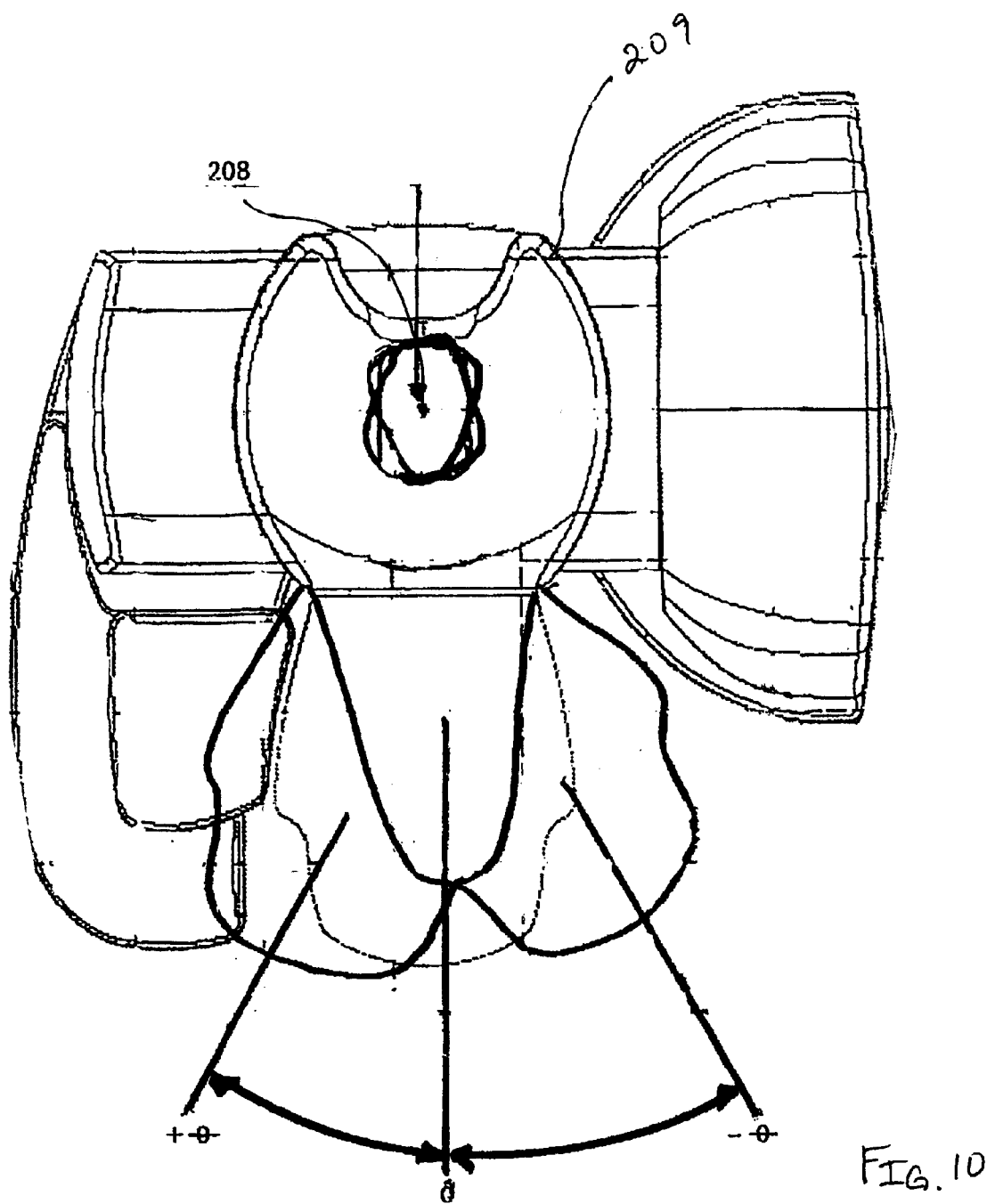
FIG. 10 illustrates the patient table rotation about an axis that passes through a point of interest.

In a typical screening process, the focal plane 2 is altered by adjusting the lens system 3 (see FIG. 1), as discussed above, to allow the diagnostician to examine the object 200 in the z dimension. It is possible that the structure 202 may coincide with the axis of rotation 208. That is, the structure may be positioned in a z axis in a location that coincides with the axis of rotation 208. FIGS. 7 and 8 illustrate a more general case in which the axis of rotation does not coincide with the focal plane 2. However, as will be described in greater detail below, the system 100 allows the structure 202 to be moved in all three dimensions so that the structure 202 coincides with the axis of rotation 208 as shown in FIG. 10. FIG. 10 is a top plan view of a patient table 209 and illustrates the patient may be rotated about the axis of rotation by rotating the entire patient table 209.

Those skilled in the art will appreciate that rotating the structure 202 about the axis of rotation 208 requires that the patient (or more specifically the object 202 to be imaged) remain in fixed position with respect to the patient table 209 and the axis of rotation 208. The patient retention mechanism (not shown) depends on the particular portion of the body to be imaged. In the examples discussed herein wherein breast imaging is performed by the system 100, compression plates (not shown) may be used to compress the breast being imaged and to retain the breast in a fixed position with respect to the patient table 209 and the axis of rotation 208.

Figure 9:
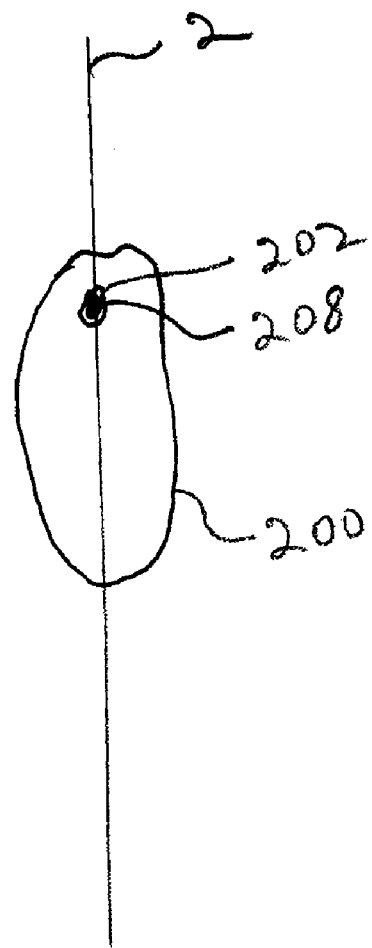
FIG. 9 illustrates positioning of the object to coincide with the axis of rotation.

Those skilled in the art will recognize that repositioning the structure 202 in the z axis so as to coincide with the axis of rotation 208 will necessitate adjustment of the lens system 3 so as to reposition the focal plane 2 so that it coincides with the axis of rotation, as illustrated in FIGS. 9–10.

Figure 11:
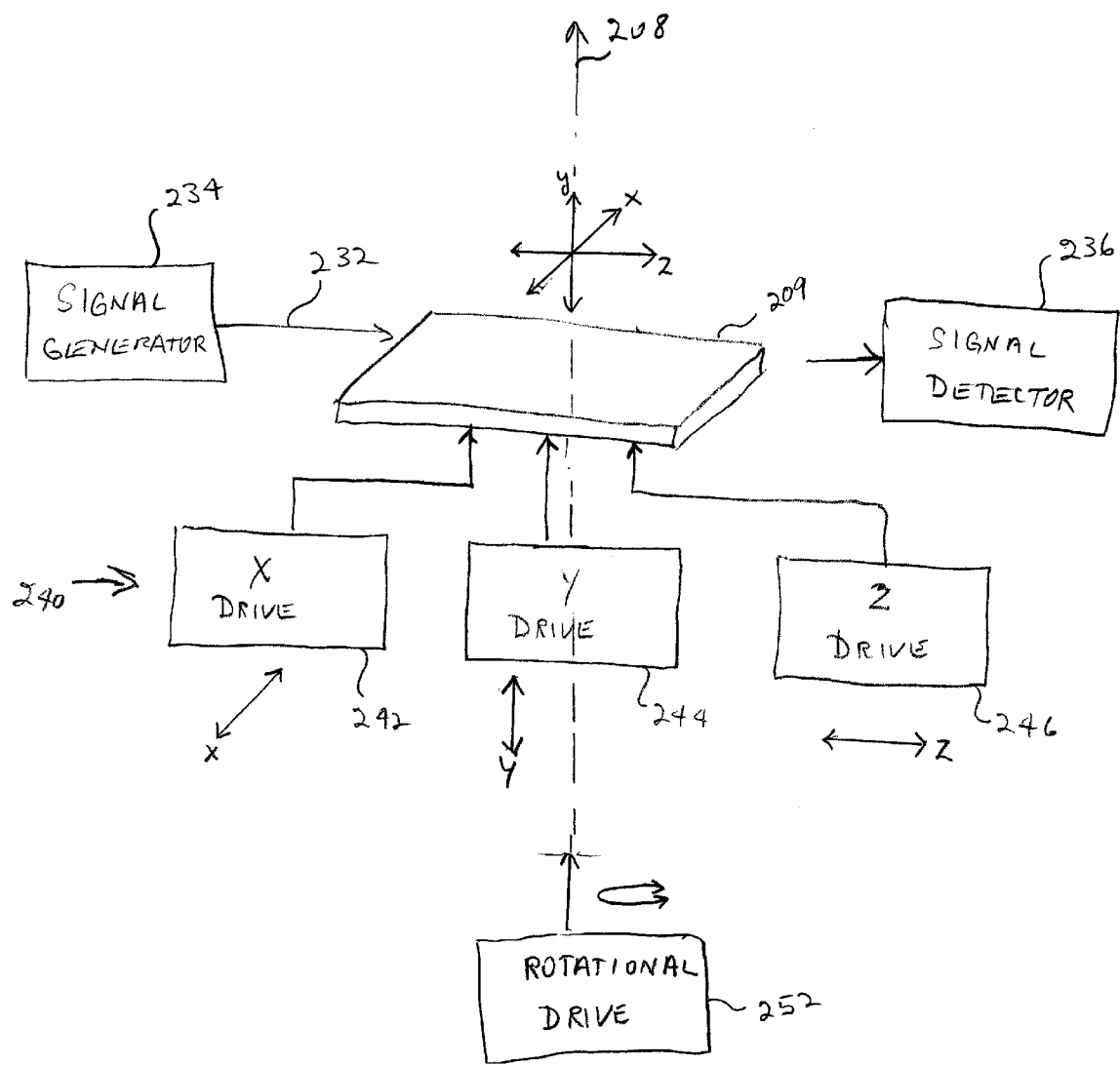
FIG. 11 diagrammatically illustrates the three-dimensional drive system used to position the imaged object at the axis of rotation and rotational drive to rotate the object above an axis of rotation.
Figure 13:
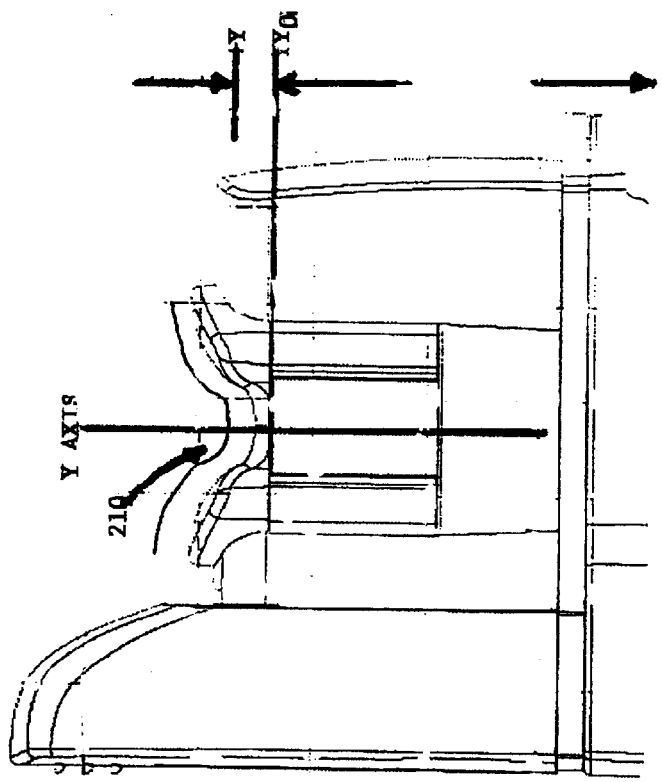
FIGS. 12 and 13 illustrate the repositioning of the patient table in three dimensional orthogonal axis.

This aspect of the system 100 is shown in diagrammatic form in FIG. 11 where the patient table 209 is used to place the patient in a comfortable position in a pathway 232 of a stimulus signal generated by a signal generator 234. For example, the signal generator 234 is an ultrasound imaging system. In an exemplary embodiment, the signal generator 234 may be a through-transmitted acoustic ultrasound imaging system. In yet another embodiment, the signal generator 234 may be part of a through-transmitted acoustic ultrasound holographic imaging system. Alternatively, the signal generator 234 may comprise an X-ray device if the imaging system is an X-ray imaging system.

A signal detector 236 detects the signal from the signal generator after it interacts with the object 200 (see FIGS. 4–9). As noted above, the signal detector 236 may be a hologram detector, such as the liquid surface hologram detector 7 shown in FIGS. 1 and 2. Alternatively, the signal detector 236 may be a known detector, such as an ultrasound detector, solid state detector, or the like if the signal generator 234 produces ultrasonic signals. The signal detector 236 may be an X-ray detector if the signal generator 234 is an X-ray device. The present invention is not limited by the specific limitation of the signal generator 234 and the signal detector 236.

The patient table 209 is coupled to a drive system 240 that comprises an x-drive 242, a y-drive 244, and a z-drive 246. For convenience in understanding the operation of the present invention, a Cartesian coordinate system is also illustrated in FIG. 11. The x-drive 242 moves the patient table in the x direction. The y-drive 244 moves the patient table 209 back and forth in the y direction, while the z-drive 246 moves the patient table back and forth in the z direction. In an exemplary embodiment, the x-drive 242, y-drive 244, and z-drive 246 are capable of moving the patient table 209 ±4.0 inches in each direction. This allows great flexibility in repositioning the patient table 209 (and the structure 202) to a desired location.

Figure 12:
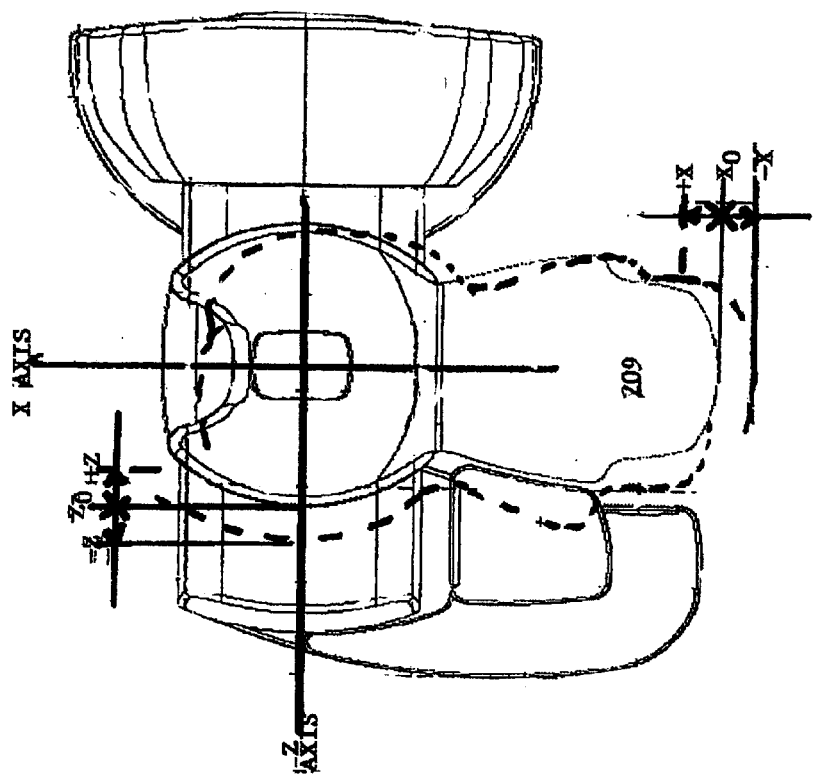

The x-drive 242, y-drive 244, and z-drive 246 may be implemented by motors or other known devices. The motors may be conventional DC motors, stepper motors, hydraulic drives, or the like. In an exemplary embodiment, the x-drive 242, y-drive 244, and z-drive 246 are stepper motors that are controlled by a conventional motor controller (not shown). The advantage of stepper motors is that the position of the patient table 209 may be precisely controlled in known increments. However, the present invention is not limited by the specific form of the drive mechanisms used to position the patient table 209. As discussed above, the patient table 209 is positionable in three dimensions. FIG. 12 is a top plan view of the system that illustrates the displacement of the patient table 209 in the x direction and the z direction. FIG. 12 is a side view that illustrates the movement of the patient table 209 in the y direction. With the mechanism described herein, the patient table 209 may be precisely positioned in a desired location. As discussed above, it is desirable to position the structure 202 (see FIGS. 4–9) at the axis of rotation 208.

The patient table 209 is coupled to a support stand (not shown), which in turn is coupled to a rotational drive 252. The rotational drive 252 rotates the support stand and patient table about the rotational axis 208. Because the patient table 209 has been manipulated such that the structure 202 is in alignment with the axis of rotation 208, the rotational drive 252 rotates the entire patient about the axis of rotation 208. In this manner, the structure 202 is properly positioned such that the signal generator 234 and signal detector 236 may image the structure 202 from various angles as the patient table 209 is rotated by the rotational drive 252.

In an exemplary embodiment, the rotational drive 252 is a DC motor having a gear mechanism to provide the necessary power to rotate the patient table 209. In an exemplary embodiment, the rotational drive 252 can rotate the patient table 209 through a range of approximately ±45°.

The diagnostician may readily activate the rotational drive 252 using conventional techniques, such as a dial, joystick, or the like, to rotate the patient device 230 and thus view the structure 200 from varying angles. In addition, the patient device 230 may be further manipulated to permit the diagnostician to view other portions of the structure 202. Thus, the system provides a convenient and simple diagnostic tool to analyze structures within an anatomical object.

The rotational system described herein is particularly useful for imaging structures from various angles. In the embodiment where the signal generator 234 and signal detector 232 are portions of an acoustic ultrasound imaging system, the depth of field (i.e., z axis resolution) can be adjusted by the lens setting selected and whether rotational or off axis imaging is employed. For a fixed single view, the depth of field can be made to be less than 1 cm or expanded to be several cm if desired. Such a process is described in U.S. Pat. No. 5,235,553. By employing multiple view and post processing techniques, this depth of field be reduced substantially below 1 cm as determined by the view and processing techniques used. The resolution in the x-y plane is much sharper and can be made to be less than one wavelength of the source being used which typically is less than 1 mm.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. In an acoustic ultrasound imaging system, a system to automatically stabilize an image detector configured to receive acoustic signals, comprising:

a base member;

a mounting platform fixedly coupled to the base member;

a leveling plate to support the image detector;

a plurality of adjustable leveling members having first and second ends, the first end of each leveling member being coupled to the mounting platform and the second ends of each leveling member being coupled to the leveling plate;

a level sensor assembly to sense an orientation of the leveling plate and generate sensor signals related thereto;

a controller, responsive to the sensor signals to generate leveling control signals; and a drive mechanism coupled to at least a portion of the leveling members and responsive to the leveling control signals to position the leveling plate at a predetermined orientation.

2. The system of claim 1 wherein the level sensor assembly and drive mechanism form a feedback circuit.

3. The system of claim 1 wherein the level sensor assembly comprises first and second level sensors positioned in a substantially orthogonal arrangement on the leveling plate to sense orientation in first and second substantially orthogonal directions.

4. The system of claim 1 wherein the plurality of adjustable leveling members comprises first and second leveling members each coupled to the drive mechanism wherein the fist and second leveling members are automatically adjusted by the drive mechanism.

5. The system of claim 4 wherein a third leveling member is manually adjustable.

6. The system of claim 5 wherein the leveling plate is an elongated plate having a central long axis, the first and second leveling members being positioned at a first end of the leveling plate on opposite sides and substantially equidistant from the long axis and the third leveling member being positioned at a second end of the leveling plate opposite the first end and substantially along the long axis.

7. The system of claim 1 wherein the drive mechanism comprises first and second drive motors coupled to first and second leveling members.

8. In an acoustic ultrasound imaging system, an apparatus to automatically stabilize an image detector configured receive acoustic signals, comprising:

a fixed mounting platform;

a leveling plate to support the image detector;

adjustable coupling means for coupling the mounting platform and the leveling plate;

sensing means for sensing an orientation of the leveling plate and generating sensor signals related thereto; and control means, responsive to the sensor signals to adjust the coupling means and thereby position the leveling plate at a predetermined orientation.

9. The apparatus of claim 8 wherein the sensing means comprises first and second sensors positioned in a substantially orthogonal arrangement on the leveling plate to sense orientation in first and second substantially orthogonal directions.

10. The apparatus of claim 8 wherein the adjustable coupling means comprises first and second leveling members each coupled to a drive mechanism wherein the fist and second leveling members are automatically adjusted by the drive mechanism.

11. The apparatus of claim 10 wherein a third leveling member is manually adjustable.

12. The system of claim 10 wherein the drive mechanism comprises first and second drive motors coupled to first and second leveling members.

13. In an acoustic ultrasound imaging system, a method for automatically stabilizing an image detector configured to receive acoustic signals, comprising:

fixedly coupling a mounting platform to a base member;

supporting the image detector with a leveling plate;

sensing an orientation of the leveling plate and generating signals related thereto; and automatically adjusting leveling members coupled to the mounting platform and to the leveling plate in response to the generated signals to thereby maintain the image detector in a predetermined orientation.

14. The method of claim 13 wherein the generated signal related to the orientation of the level sensor assembly and drive mechanism form a feedback circuit.

15. The method of claim 13 wherein sensing the orientation of the leveling plate comprises sensing orientation in first and second substantially orthogonal directions.

16. The method of claim 13 wherein adjusting the leveling members comprises activating a drive mechanism coupled to first and second leveling members.

* * * * *

UNITED STATES PATENT AND TRADEMARK OFFICE
CERTIFICATE OF CORRECTION

| | | |
|---|---|---|
| PATENT NO. | : 6,544,186 B1 | Page 1 of 1 |
| APPLICATION NO. | : 09/988839 | |
| DATED | : April 8, 2003 | |
| INVENTOR(S) | : Jerod O. Shelby et al. | |

It is certified that error appears in the above-identified patent and that said Letters Patent is hereby corrected as shown below:

Title Page
Inventors (75), "Jerod O. Shelby, West Richland, WA (US); Barbara A. Fecht, Richland, WA (US); Todd F. Garlick, Pasco, WA (US); George F. Garlick, Richland, WA (US); Victor I. Neeley, Kennewick, WA (US)" should read as --Jerod O. Shelby, West Richland, WA (US); Todd F. Garlick, Pasco, WA (US); George F. Garlick, Richland WA (US)--.

Signed and Sealed this

Thirtieth Day of January, 2007

JON W. DUDAS
*Director of the United States Patent and Trademark Office*